Figure 9:
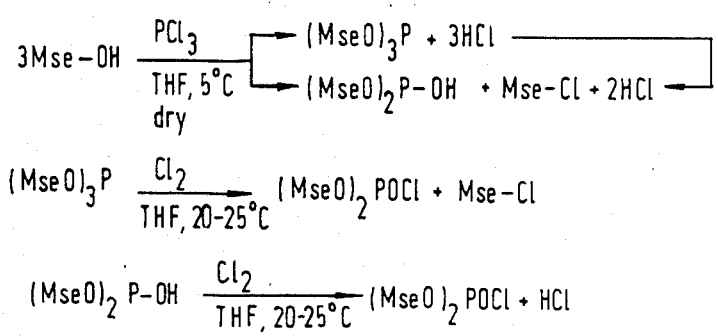

United States Patent [19]

Tesser et al.

[11] Patent Number: 4,692,542
[45] Date of Patent: Sep. 8, 1987

[54] PHOSPHORYLATING AGENT

[75] Inventors: Godefridus I. Tesser; Christianus A. A. Claesen, both of Nijmegen, Netherlands

[73] Assignee: Stichting Katholieke Universiteit, Nijmegen, Netherlands

[21] Appl. No.: 622,571

[22] Filed: Jun. 20, 1984

[30] Foreign Application Priority Data

Jul. 1, 1983 [NL] Netherlands .......................... 8302353

[51] Int. Cl.$^4$ .......................... C07F 9/146; C07F 9/14; C07F 9/65
[52] U.S. Cl. .................................. 558/184; 548/111; 548/114; 548/116
[58] Field of Search .................. 260/948; 558/184; 548/111, 114, 116

[56] References Cited

FOREIGN PATENT DOCUMENTS 131993 1/1985 European Pat. Off. .

OTHER PUBLICATIONS

Clark et al, "Angew. Chem." 76, (1964) pp. 704–712.
Slotin, "Synthesis," 1977, pp. 737–752.
Fourrey et al, "Tetrahedran Letters," 22, (1981) pp. 729–732.
van der Marel et al, "Tetrahedran Letters," 22, (1981) pp. 3887–3890.
van der Marel et al, "Neuleic Acid Research", 10, (1982), pp. 2337–2351.
Knorre et al, "Phosphorus Chemistry Directed Toward Biology", (1979) pp. 13–31.
van der Marel et al, "Tetrahedran Letters", 22, (1981) pp. 1463–1466.

Primary Examiner—Anton H. Sutto
Attorney, Agent, or Firm—Weingarten, Schurgin, Gagnebin & Hayes

[57] ABSTRACT

The invention relates to phosphorylating agents containing at least one protected hydroxyl group and at least one leaving group. According to the invention, a methylsulphonylethyl group (Mse) is used as the hydroxyl protecting group. Typical examples of such phosphorylating agents are the compounds $(MseO)_2POL$, $(MseO)POLL'$, $(MseO)_2PL$ and $(MseO)PLL'$, in which L and L' are leaving groups. The invention also relates to processes for preparing these phosphorylating agents and processes for the phosphorylation of organic hydroxyl or amine compounds, in particular nucleosides and (poly)nucleotides.

4 Claims, 22 Drawing Figures

Fig. 1
PRIOR ART
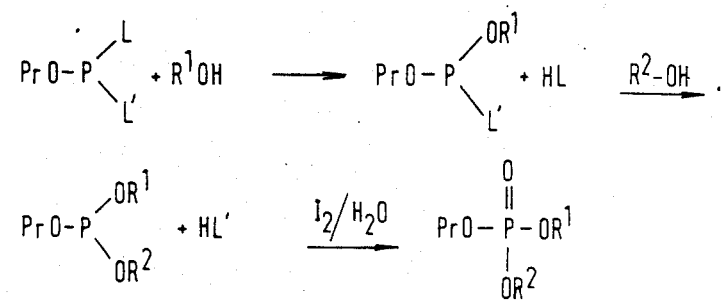
Fig. 2
PRIOR ART
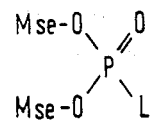 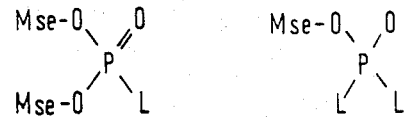 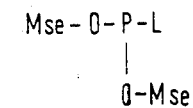
Fig. 3　　Fig. 4　　Fig. 5
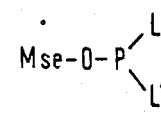 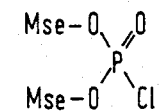 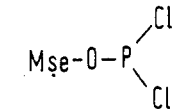
Fig. 6　　Fig. 7　　Fig. 8

PHOSPHORYLATING AGENT

This invention relates to a phosphorylating agent, containing at least one protected hydroxyl group and at least one leaving group. The invention also relates to a process for preparing such a phosphorylating agent, and to a process for the phosphorylation of an organic hydroxyl or amine compound.

One important application of phosphorylating agents is the synthesis of DNA and RNA fragments which can be used in biological research. A survey of the methods of preparing such fragments is given in Tetrahedron 34, 3143-3179 (1978). Such fragments are called oligonucleotides. They are polyphosphoric acid esters, in which the 3'-hydroxyl group of a nucleoside moiety is connected to the 5'-hydroxyl group of another nucleoside moiety via a phosphoric acid diester compound. Commonly when two nucleoside moieties are coupled the 3'-hydroxyl group of one moiety is phosphorylated to form a phosphoric acid ester which is capable of forming an ester compound with the 5'-hydroxyl group of the other moiety.

This synthesis technique, which has been introduced by Eckstein and Riszk in Angew. Chemie 79, 684-685 (1976), is known as the phosphotriester approach.

The phosphorylating strategy used therein is shown in FIG. 1. In it, Pr and Pr' represent hydroxyl protecting groups, L represents a leaving group, and R—OH represents a monovalent nucleoside derivative, nucleotide derivative, or polynucleotide derivative.

As the technique of synthesis is not very efficient for the preparation of longer-chain polynucleotides, due to the relatively slow reaction of activated phosphates with hydroxyl groups, Letsinger, Finnan and Lunsford in J.A.C.S. 97, 3278-3279 (1975) proposed for the synthesis strategy shown in FIG. 2. In it, Pr represents a hydroxyl protecting group, L and L' represent leaving groups, and $R^1$—OH and $R^2$—OH represent nucleoside derivatives, nucleotide derivatives, or polynucleotide derivatives that have to be interconnected. In this case the phosphorylating agent is an activated phosphite triester. The product after the coupling of the hydroxyl compounds is a phosphite triester, which with a very high yield can be oxidized with an iodine-water mixture to form a phosphate triester. This method of synthesis is known as the phosphite triester method.

In the nucleoside moieties, all other reactive groups should generally be protected, that is to say, in one nucleoside moiety all reactive groups except for the 3'-hydroxyl group, and in the nucleoside moiety all reactive groups except for the 5'-hydroxyl group. The phosphorylating agent used should preferably be such a phosphoric acid or phosphorus acid derivative that after the accomplishment of the diester bond between two nucleosides the third hydroxyl group of the phosphoric acid or phosphorous acid is protected. In fact, the principal objection of a nonprotected phosphorus-linked hydroxyl group is that during a next phosphorylation it can react with the phosphorylating agent (see the above article in "Tetrahedron"). It must be possible for the protective group, however, to be removed at the end of the synthesis without damage to the internucleotide bonds and without the purine or pyrimidine bases being split off.

The hydroxyl protecting groups used for the phosporylating agent are generally groups removable in a basic medium, such as the phenyl group, the o-chlorophenyl group, the 2,4-dichlorophenyl group, the 2,2,2-trichloroethyl group, and the $\beta$-cyanoethyl group, in the case of phosphate triester phosphorylating agents, and the o-chlorophenyl group, the 2,2,2-trichloroethyl group, and the methyl group in the case of phosphite triester phosphorylating agents. Generally speaking, the removal of these groups in a basic medium, referred to herein as deprotection, is a cumbersome or lengthy affair. Thus in case phenyl is the protected group, deprotection requires an 8-hour treatment at 20° C. with a 4:1 mixture of 0.125N NaOH/dioxane; in the case of o-chlorophenyl a treatment with 0.1-0.125N NaOH for some hours; in the case of 2,4-dichlorophenyl a treatment with 5 equivalents of oximate in $Et_3N$/dioxane/$H_2O$ for 1-10 hours; and in the case of 2,2,2-trichloroethyl a treatment with zinc dust in boiling pyridine for 0.5 hour.

It has now been found that the methylsulphonylethyl group $CH_3$—$SO_2$—$CH_2$—$CH_2$— (referred to herein as Mse) is a highly suitable hydroxyl protecting group for phosphorylating agents, which under acid conditions is highly stable, and under basic conditions can be removed quite fast and with facility, and if desired selectively.

The invention accordingly provides a phosphorylating agent of the kind described, which is characterized by containing at least one hydroxyl group that is protected by methylsulphonylethyl.

More specifically the invention provides a phosphorylating agent which satisfies any of the formulae shown in FIGS. 3-6 in which Mse represents the methylsulphonylethyl group $CH_3SO_2CH_2CH_2$— and L and L' represent leaving groups.

In principle, all conventional leaving groups are suitable as leaving groups L and L', but preferred groups are chloro; 1,2,4-triazolyl; tetrazolyl; phthalimidooxy; succinimidooxy and benzotriazolooxy.

Most preferred is a phosphorylating agent satisfying the formula shown in FIG. 7 (phosphate-triester phosphorylating agent) and a phosphorylating agent satisfying the formula shown in FIG. 8 (phosphite-triester phosphorylating agent).

Although, in the following examples, the invention will be illustrated with reference to these two specific phosphorylating agents, it will be clear that the invention is not limited to these two preferred embodiments, and that, under circumstances, the use of, for example, leaving groups other than chlorine is preferred. Specifically, when a phosphite triester is used, it may be desirable for the chlorine, which causes a high reactivity, but at the same time a low selectivity, to be replaced by a leaving group such as a triazolyl or a tetrazolyl group, whereby selectivity (O-phosphorylating of the nucleoside sugar instead of N-phosphorylating of the nucleoside base) of the phosphorylating agent is improved.

The Mse group has not been previously proposed as a protecting group. From the peptide chemistry, however, the methylsulphonyl ethyloxycarbonyl group $CH_3SO_2CH_2CH_2OCO$— (Msc group) is known as an amino protecting group (Tesser and Balvert-Geers in Int. J. Peptide Protein Res. 7, 295-305 (1975). Compounds containing this Msc group are synthesized starting from 2-methylsulphonyl ethyl alcohol, which itself can be prepared by the catalytic oxidation of 2-methylmercaptoethanol with hydrogen peroxide and sodium tungstenate. The Msc function is an extremely acid-stable protecting group which can be rapidly removed under basic conditions.

The phosphorylating agents according to the present invention can be prepared in a manner known for analogous compounds. The skilled worker will generally be able to determine what procedures of synthesis are eligible, and which of these are particularly suitable for the synthesis of a selected phosphorylating agent according to the present invention.

A particular method of preparing a phosphorylating agent having the formula shown in FIG. 7 is one in which 2-methylsulphonyl ethyl alcohol in an inert solvent, preferably dry tetrahydrofuran, is successively reacted with $PCl_3$ and $Cl_2$. Preferably, the treatment with $PCl_3$ is effected at a low temperature of 0°–10° C., most preferably about 5° C., and the subsequent treatment with $Cl_2$ is effected at a temperature of 15°–30° C., most preferably 20°–25° C.

In FIG. 9, the reactions are shown which may take place in this method of synthesis. In the first step, there is formed a two-phase system between tetrahydrofuran and an oil, which may consist of tris-(Mse) phosphite or bis-(Mse) phosphite. In addition, the substance first-mentioned may have reacted with HCl to form the second. The true nature of the intermediary phosphite has not yet been determined with certainty. By treating the two-phase system produced in the first step with $Cl_2$, the compound of formula 5 can be obtained in high yield of approx. 90%.

A particular method of preparing a phosphorylating agent having the formula shown in FIG. 8 is one in which 2-methylsulphonyl ethyl alcohol, with exclusion of water, is refluxed with stirring in excess $PCl_3$ until no HCl escapes any longer, whereafter the excess of $PCl_3$ is distilled off and the remaining oily liquid is distilled at a reduced pressure. Preferably, the 2-methylsulphonylethyl alcohol is refluxed at 90°–100° C. in a four-fold to eight-fold excess, most preferably in a six-fold excess of $PCl_3$. The 2-methylsulphonylethyl alcohol is, for example, added dropwise in a pure form under ultradry conditions and at room temperature to a six-fold excess of $PCl_3$, whereafter the mixture is refluxed at 90°–100° C. in the absence of a solvent or base and with vigorous stirring. When no more HCl escapes, the excess of $PCl_3$ is distilled off. The remainder is a highly hygroscopic oily liquid, which reacts violently with water and, in addition to the desired reaction product contains one or more unknown contaminations. When this liquid is distilled in a "Kugelrohr" (bulbed tube) at a reduced pressure, a clear oily liquid is distilled at 0.1 mm Hg and 160° C., which in addition to the desired reaction product contains a minute amount of impurities. Under the same conditions, but at 200° C., a clear oily liquid containing even less impurities is distilled. The yield of the desired compound having the formula shown in FIG. 8 is, after distillation, approx. 56%, calculated on the basis of the 2-methylsulphonylethyl alcohol used as the starting material. Naturally, the compound having the formula shown in FIG. 8 can be isolated in still purer form using known techniques.

The phosphorylating agents according to the invention can be used for phosphorylating organic hydroxyl and amine compounds. Examples are sugars, e.g. glucose and myo-inositol; alcohols, such as p-nitrobenzyl alcohol and pyrocatechol; and secondary amines, such as morpholine. Alcoholates, such as sodium paranitrophenolate, can also be phosphorylated using the present phosphorylating agents. When the phsophorylating agent used in a phosphite triester, the phosphorylated product can be oxidized in known manner to a phosphate triester, for example, by means of iodine in water.

The phosphorylating agents according to the invention are particularly intended and suitable for the phosphorylation of nucleoside derivatives, nucleotide derivatives, and polynucleotide derivatives having a free 3'-hydroxyl group or a free 5'-hydroxyl group, and in which the other reactive groups, e.g. hydroxyl groups and amine groups, if present, are protected.

For the deprotection, two particularly suitable methods have been developed. The first method uses a deprotection mixture containing NaOH and methanol, in particular 14:5:1 mixture (ratio by volume) of dioxane/methanol/4N NaOH. This mixture contains 5% by volume of water and has a NaOH concentration of 0.2M. By means of a suitable selection of the number of equivalents of base with which the compounds to be protected are contacted, it is possible to remove the Mse group or Mse groups completely in a short period of time, or if the compound contains two Mse groups, if desired removing selectively only one of these Mse groups. Thus, it will often be possible, by using only 1.1 equivalents of base to remove selectively only one of the Mse groups, while when, for example, 3 equivalents of base are used both Mse groups are removed completely. Deprotection generally requires a period of treatment in the order of a few seconds to a few minutes, for example 10 seconds when 3 equivalents of base are used and 2 minutes in the case of 1.1 equivalents of base.

The second deprotection procedure uses ammonia, either as a concentrated solution of ammonia in methanol, or as ammonia gas which is passed through a solution of the compound to be deprotected in acetonitrile or tetrahydrofuran. By this method, too, selective deprotection is possible. Using a concentrated (1:1) solution of ammonia in methanol, a selective removal of only one Mse group can be realized at 21° C. within about 1–2 minutes; the complete removal of both Mse groups requires more than 30 minutes. When ammonia gas is passed through a solution of the compound to be deprotected in acetonitrile or tetrahydrofuran, a selective deprotection of one Mse group at 21° C. requires approx. 1 to 1.5 hours. This deprotection can be greatly accelerated, however, by conducting the reaction in the presence of water. When, for example, 2% by volume of water is added to the solution, the selective deprotection is found to be accomplished in about 30 minutes.

The invention is illustrated by the following experimental section.

1. GENERAL PRECAUTIONS

Reactions in which use is made of phosphochloridates or phosphodichloridites should be carried out under ultra dry conditions. In these cases, therefore, use was made of glassware which had been dried at 100° C. for some hours or overnight and then cooled in exsiccators over $P_2O_5$ or NaOH pellets. Solvents used in the above reactions were dried as follows:

Tetrahydrofuran, THF. The absolute quality was dried and rendered peroxide-free by distillation from calcium hydride ($CaH_2$) just prior to use, except in reactions in which use was made of methylsulphonylethyl-phosphodichloridite having the formula shown in FIG. 8, where absolute THF was first passed over a column of activated alumina (Alumina-Woelm B-Super I, 04571-b1159), followed by drying on Na metal for a minimum period of 4 hours, excluding daylight.

Acetonitrile, CH$_3$CN. Technical grade was distilled from P$_2$O$_5$ just prior to use.

Pyridine, C$_6$H$_5$N. Pyridine was kept in a well-sealed bottle on CaH$_2$ and distilled from CaH$_2$, excluding moisture, just prior to use.

Reagents were rendered free from water as follows:

Methylsulphonylethyl alcohol, Mse—OH, was dissolved (60° w/v) in absolute ethanol (Baker), whereafter the ethanol was removed at a reduced pressure in a rotational evaporator (bath temperature 40°–50° C.). The treatment was repeated three times. Traces of ethanol were removed overnight in a freeze drier.

Phosphorus trichloride, PCl$_3$, was distilled with exclusion of moisture just prior to use.

Figure 10:
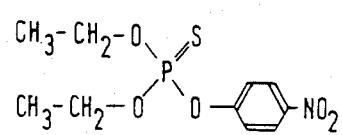
Figure 11:
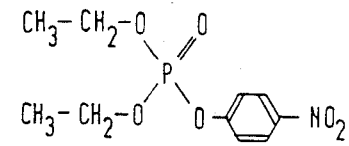

Furthermore, a caution is appropriate here for the possible neurotoxicity of the phosphate esters synthesized. Dialkoxy-phosphochloridates are notorious neurotoxic materials, while many of the neutral phosphoric acid esters described herein exhibit structural similarities to the agricultural pesticides Parathion (FIG. 10) and especially Paraoxon (FIG. 11).

Furthermore many phosphites are notorious poisonous substances.

2. ANALYTICAL TECHNIQUES (a) Thin-layer chromatography (TLC)

TLC was performed on kiesel gel sheets with U.V. indicator. In each case 2γ of the sample to be analyzed was applied. (1γ is 1 μl of a 1% solution). Detection was effected with 254 nm U.V. light.

The coding of the mobile phases used is as follows.

| mobile phase | Code |
|---|---|
| CHCl$_3$:CH$_3$OH 2:1 | A |
| CHCl$_3$:CH$_3$OH 9:1 | B |
| n-butanol:acetic acid:water 4:1:1 | C |
| Isopropyl alcohol:NH$_3$:water 4:1:1 | D |
| Isopropyl alcohol:NH$_3$:water 7:1:2 | E |

(b) NMR spectra $^1$H-NMR spectra were made on a Hitachi 60 MHz or on a Bruker 100 MHz apparatus.

$^{31}$P-NMR spectra were also made using the latter machine.

(c) IR spectra

Infrared spectra were taken with a Perkin-Elmer (KBr pellets). Hygroscopic solids were rubbed on a KBr pellet and subsequently sandwiched with a second KBr pellet.

(d) Determination of hydrolysable chlorine

Requisites:

Isopropyl alcohol p.a.; 0.1% bromophenol blue in abs. ethanol;

2N HClO$_4$ solution; diphenyl carbazone, 0.5% in abs. ethanol;

0.01M Hg (NO$_3$)$_2$ solution.

Procedure:

10–40 mg of the substance to be determined was weighted with great accuracy and subsequently taken up in 50 ml isopropyl alcohol p.a. In the case of highly reactive substances, care was taken that no HCl gas escaped during this treatment. 10 ml distilled water was added, and thereafter 0.2 ml bromophenol blue solution was added. One drop of the 2N HClO$_4$ solution now gave a change to yellow.

Subsequently 0.2 ml of diphenylcarbazone solution was added and the wall of the titration vessel was rinsed with 30 ml iospropyl alcohol p.a. The solution was titrated with 0.01M Hg (NO$_3$)$_2$ solution in distilled water to a colour change to violet.

Titer setting of the Hg (NO$_3$)$_2$ solution was effected with p.a. grade KCl.

3. SYNTHESIS OF BIS-(MSE)-PHOSPHOCHLORIDATE (FIG. 7)

In a 250 ml three-neck flask, equipped with a thermometer, a calcium chloride tube, a 50 ml drop funnel and an overhead stirrer with a gas-tight paraffin-lubricated sliding bearing, 24.83 g (0.200 mole) Mse—OH in 50 ml tetrahydrofuran was introduced. To this solution, 9.16 g (0.0667 mole) PCl$_3$ in 25 ml tetrahydrofuran was added drop-wise with vigorous stirring. The dropping rate was approx. 1 drop per 1.5 sec., and the temperature of the reaction mixture was maintained at 5° C. by means of an ice and salt mixture.

Halfway the addition of PCl$_3$, a two-phase system was formed. When all PCl$_3$ had been added, stirring was continued for another hour, whereafter the two-phase system was allowed to stand overnight at 21° C. (For this purpose the three-neck flask was protected from daylight with aluminum foil).

Subsequently, with vigorous stirring, via two washing bottles with 98% H$_2$SO$_4$, gaseous chlorine was introduced into the two-phase system. The combination of cooling with ice and the rate of chlorine gas introduction during this exothermic reaction were selected so that the temperature remained between 20° and 25° C. After chlorine gas introduction for about 13 minutes, the two-phase system disappeared, and a clear solution, coloured light-yellow by chlorine gas, was formed. After chlorine gas introduction for about 80 minutes, the solution suddenly became turbid from the crystallization of bis-(Mse)-phosphochloridate. During the next five minutes more and more of the product was crystallized, while the exothermia of the system clearly decreased. This latter was compensated for by reducing cooling. After 90 minutes' chlorine gas introduction, the yellow colour of the chlorine disappeared from the solution within two further minutes.

After 120 minutes, the reaction was virtually completed; the colour of the chlorine gas required approx. 5 more minutes to disappear. At this point chlorination was discontinued. "Overchlorination" often led to a poor-quality product.

After subsequently passing dry N$_2$ gas through the mixture for 1 hour to remove HCl gas, the product was collected on a G-3 glass filter. Thereafter it was washed on the filter with dry tetrahydrofuran, and then stirred twice with 80 ml tetrahydrofuran and re-filtered.

Subsequently the product was subjected to an oil-pump vacuum in a exsiccator over P$_2$O$_5$ for 3–4 hours to remove HCl and tetrahydrofuran. Thereafter 19.24 g of loose, compact white powder was obtained. The substance was kept in portions of 2 g in preparation bottles wound with parafilm. These bottles were placed in pots with calcined calcium chloride, which, again well wrapped in parafilm, were stored at 4° C.

bis-(Mse)-phosphocloridate (MW: 328.75): Yield 19.24 g (0.585 mole) i.e. 88% (PCl$_3$) or 59%

(Mse—OH). Melting range: 92°–94° C. Hydrolysable chlorine: 98 mole % (theory: 100 mole %). $^1$H-NMR:

| function | group | δ (ppm) | mult. | J (Hz) | number of prot. |
|---|---|---|---|---|---|
| Mse- | CH$_3$— | 3.05 | S | — | 6 |
| | β-CH$_2$— | 3.60 | T | $^3J_{H-H}$, 5.5 | 4 |
| | α-CH$_2$— | 4.72 | "Sext" | $^3J_{H-H}$, 5.5 $^3J_{P-H}$, 8.5 | 4 |

Mult. stands for the multiplicity of the signal: S: singlet D: doublet; T: triplet; etc.

4. SYNTHESIS OF BIS-(MSE)-PARANITROPHENYL PHOSPHATE (FIG. 12)

To a solution of 3.616 g (0.011 mole) of bis-(Mse)-phosphochloridate in 110 ml acetonitrile in a 250 ml bulb flask, 1.777 g (0.011 mole) of sodium paranitrophenolate (dried over P$_2$O$_5$ in vacuo at 60° C., until orange-red without traces of yellow) was added, whereafter the flask was immediately re-sealed. The orange-red sodium paranitrophenolate was gradually dissolved with stirring at room temperature, and a precipitate of NaCl was separated.

After stirring for about 20 minutes, all sodium paranitrophenolate was dissolved, and the resulting NaCl was filtered off.

After evaporation of the filtrate, a yellow oil was formed, from which the residues of acetonitrile were removed by means of an oil pump.

After scratching the wall of the flask with a spatula, the oil crystallized spontaneously.

Recrystallization from methanol produced 4.07 g white crystals.

bis-(Mse) paranitrophenyl phosphate (MW: 431.4) Yield 4.07 g (0.0094 mole), 85.5%. Melting range: 107°–108° C. Rf value in mobile phase A: 0.78. Elemental analysis: C: 33.20–33.21; H: 4.11–4.16; N: 3.12—3.12 theory: C: 33.41; H: 4.21; N: 3.25. $^1$H-NMR:

| function | group | δ (ppm) | mult. | J (Hz) | number of prot. |
|---|---|---|---|---|---|
| Mse | CH$_3$— | 3.05 | S | — | 6 |
| | β-CH$_2$— | 3.50 | T | $^3J_{H-H}$, 5.5 | 4 |
| | α-CH$_2$— | 4.57 | "sext" | $^3J_{H-H}$, 5.5 $^3J_{P-H}$, 7.0 | 4 |
| Aryl- | Aryl- | 7.92 | 2x D | $^3J_{H-H}$, 9.0 | 4 |

IR:

| function | group | wave number and strength of signal |
|---|---|---|
| Mse- | —SO$_2$— | 1315 cm$^{-1}$ (M), 1135 and 1120 cm$^{-1}$ (S) |
| Aryl- | Aryl-H | 1600 cm$^{-1}$ (M) |
| | Aryl-NO$_2$ | 1520 and 1355 cm$^{-1}$ (S) |
| Phosphate | P=O | 1290 cm$^{-1}$ (S) |
| | P—O—Aryl | 1170 cm$^{-1}$ (W) |
| | P—O—Alkyl | 1035 cm$^{-1}$ (S) |

Relative strengths: W: weak; M: medium; S: strong.

5. KINETICS OF THE DEPROTECTION OF BIS-(MSE)-PARANITROPHENYLPHOSPHATE WITH NaOH/METHANOL 86.3 mg (200 μmole) bis-(Mse)-paranitrophenyl phosphate was dissolved with heating in 2 ml dioxane. Of this solution, 50 μl portions (total: 5 μmole ester) were pipetted into Eppendorf centrifuge vessels. The deprotection mixture consisted of 0.25 ml dioxane in 1.875 ml methanol, to which had been added:

0.375 ml 4N NaOH (Solution A) or:
0.378 ml 2.67N NaOH (Solution B) or:
0.375 ml 2.0N NaOH (Solution C) or:
0.375 ml 1.47N NaOH (Solution D).

Figure 12:
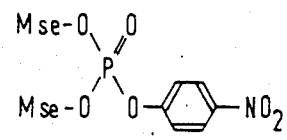

The addition of 25 μl of the above deprotection mixture A, B, C or D to the vessel containing 5 μmole of ester in 50 μl dioxane resulted in a mixture of dioxane:methanol:NaOH/H$_2$O of 14:5:1 with a relative base concentration of: 3 equivalents (A), 2 eq. (B), 1.5 eq. (C) or 1.1 eq (D). The deprotection mixture was added to the ester solution with a Hamilton microsyringe, immediately followed by mixing with a Vortex mixer. After the prescribed reaction period the base was immediately quenched with 0.1 ml of a solution of 0.2M acetic acid in methanol. Thin-layer chromatography was performed with 2 μl of the resulting solution on kiesel gel plates with U.V. indicator in mobile phase A, R$_f$ values: Paranitrophenyl phosphate, bis Na salt (FIG. 14): O; mono-(Mse)-paranitrophenyl phosphate, Na$^+$ salt (FIG. 13): 0.24; bis-(Mse)-paranitrophenyl phosphate (FIG. 12): 0.78.

Figure 13:
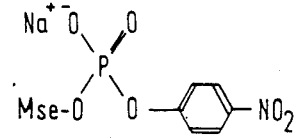
Figure 14:
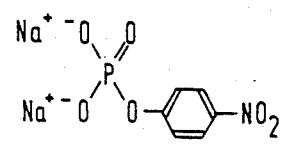

The thin-layer chromatograms showed that when 1.1 eq. base was used the compound shown in FIG. 13 was selectively obtained after 120 sec.; when 3 eq. base was used only the compound shown in FIG. 14 was demonstrable after a period as short as 10 sec. When 1.5 and 2 eq. base were used, a mixture of two compounds, in which the compound shown in FIG. 14 was predominant, was obtained after 300 and 120 sec., respectively.

6. DEPROTECTION OF BIS-(MSE)-PARANITROPHENYL PHOSPHATE TO MONO-(MSE)-PARANITROPHENYL PHOSPHATE, Na$^+$ SALT AND PARANITROPHENYL PHOSPHATE, BIS Na$^+$ SALT (a) Mono-(Mse)-paranitrophenyl phosphate, Na$^+$ salt (FIG. 13)

To a solution of 2.66 g (0.0062 mole) of bis-(Mse)-paranitrophenyl phosphate in 61.25 ml dioxane 92.75 ml of deprotection mixture (Dioxane:methanol:1.4N NaOH/H$_2$O=14:5:1) was slowly added dropwise at room temperature with vigorous stirring. After 8 minutes the addition was completed, and the amount of base added was 1.05 equivalents. Thereafter the mixture was quenched with three drops of acetic acid to colour change of the released trace of paranitrophenyl (yellow→colourless). Evaporation of the reaction mixture in a rotary evaporator produced a yellow oil which after the addition and reevaporation of distilled water became crystalline. The yellow crystals were decolourized by repeated washing with tetrahydrofuran.

Mono-(Mse)-paranitrophenyl phosphate, Na$^+$ salt. (MW: 347.21): Yield 1.95 g (0.0562 mole), 91%. Chromatographically pure, mobile phase A: R$_f$ 0.24.

(b) Paranitrophenyl phosphate, bis-Na$^+$ salt (FIG. 14)

To a solution of 380 mg (0.00088 mole) of bis-(Mse)-paranitrophenyl phosphate in 8.75 ml dioxane, 13.25 ml of deprotection mixture (Dioxane:methanol:4N NaOH/H$_2$O=14:5:1) was added dropwise at room temperature with vigorous stirring. A precipitate was formed virtually immediately. The addition took 15 seconds, and after reacting for a total period of 20 seconds, the mixture was quenched with about 0.15 ml acetic acid to colour change of paranitrophenol. The precipitate was filtered and washed with dioxane, whereafter it was placed in a vacuum exsiccator at 1 mm Hg for one hour to remove dioxane and any acetic acid.

Paranitrophenyl phosphate, bis Na+ salt: Yield 0.260 g (0.00099 mole), 112% (water of crystallization!). $R_f$ value in mobile A: 0. IR:

| function | group | wave number (cm$^{-1}$) and strength |
|---|---|---|
| Aryl- | Aryl-H | 1600 (S) |
|  | Aryl-NO$_2$ | 1500 (S) and 1355 (S) |
| Phosphate- | P=O | 1290 (S) |
|  | P—O—Aryl | 1270 (S, shoulder) |

For characterization, the above bis-Na+ salt was converted into the bis-cyclohexlammonium salt of paranitrophenyl phosphate. Cyclohexylammonium chloride was prepared by adding dropwise to a solution of cyclohexylamine in diethylether an anhydrous solution of HCl in ethylacetate until a thick pasty precipitate formed; crystallization from ethanol produced pure cyclohexylammonium chloride.

A solution of 0.261 g (0.00194 mole) cyclohexylammonium chloride in 2.3 ml distilled water was added to a solution of 0.230 g (0.00097 mole) of paranitrophenyl phosphate, bis-Na+ salt in 2.3 ml distilled water, whereby the biscyclohexylammonium salt of paranitrophenyl phosphate precipitated immediately; the precipitate was washed a few times with distilled water.

Yield was 0.312 g (0.000747 mole), which is 77% on the basis of the bis Na+ salt. This implies an actual yield of bis-Na+ salt of 77%×112%+86%.

Paranitrophenyl phosphate, bis-cyclohexylammonium salt: Melting range 199°–201° C. (Theory: 199°–200° C.). Elemental analysis: C: 51.37–51.50; H: 7.61–7.70; N: 9.76–9.85. Theory: C: 51.79; H: 7.73; N: 10.07. IR:

| function | group | wave number (cm$^{-1}$) and strength |
|---|---|---|
| Aryl- | Aryl-H | 1590 (S) |
|  | Aryl-NO$_2$ | 1510 (S) and 1340 (S) |
| Phosphate | P=O | 1265 (S) |
|  | P—O—Aryl | 1165 (M) |
| Cyclohexyl-ammonium | —CH$_2$— | 1455 (M) |

7. ENZYMATIC HYDRDYSIS OF PARANITROPHENYL PHOSPHATE, BIS-Na+ SALT, WITH ACID PHOSPHATASE.

For a qualitative characterization of the bis-Na+ salt of paranitrophenyl phosphate, this salt was subjected to enzymatic hydrolysis by an acid phosphatase isolated from potatoes.

Preparation of acid phosphatase

A potato was ground and the resulting pulp centrifuged in a Labofuge 6000 at 3000 rpm for 5 minutes. To 15 ml of the supernatant, 0.1 g calcium acetate was added to precipitate any phosphate, followed by re-centrifugation at 3000 rpm, now for 20 minutes. The resulting supernatant is referred to as the "acid-phosphatase solution".

Enzymatic hydrolysis 60 mg paranitrophenyl phosphate, bis-Na+ salt was dissolved in 50 ml sodium acetate buffer, pH 5.0 (3 ml acetic acid in 1 l distilled water, adjusted with 4N NaOH). In four test tubes, 5 ml portions of the above buffered solution were introduced, whereafter 0.2, 0.4 and 0.8 ml acid-phosphatase solution was added to three of these tubes. To one of the tubes, 0.8 ml pre-boiled acid-phosphatase solution was added (control).

All tubes were subsequently incubated at 37° C. for 30 minutes. After this period all solutions, except for the control, had clearly coloured yellow as a result of the release of paranitrophenol.

Figure 15:
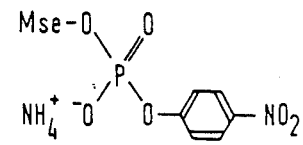

8. DEPROTECTION OF BIS-(MSE)-PARANITROPHENYL PHOSPHATE WITH NH$_3$ GAS TO MONO-(MSE)-PARANITROPHENYL PHOSPHATE, NH$_4$+ SALT (FIG. 15)

Through a solution of 1.92 g (0.00445 mole) of bis-(Mse)-paranitrophenyl phosphate in 50 ml technical-grade acetonitrile in a 100 ml bulb flask, NH$_3$ gas was slowly introduced by means of a Pasteur pipet at room temperature. After about thirty minutes, a solid began to crystallize from the solution. After 45 minutes the passage of NH$_3$ gas was discontinued, and the flask with the reaction mixture was sealed. After standing for another 45 minutes at room temperature, the precipitate was collected on a G-3 glass filter and washed with acetonitrile cooled to 0° C. Recrystallization from acetonitrile produced 1.22 g needle-shaped, white crystals.

Mono-(Mse)-paranitrophenyl phosphate, NH$_4$+ salt, (MW: 341.25) Yield: 1.22 g (0.00358 mole), 81%. Melting range: 142°–143° C. $R_f$ value in mobile phase A: 0.24. Elemental analysis: C: 31.51–31.66 H: 4.39–4.39 N: 8.01–8.06. Theory: C: 31.58 H: 8.18. $^1$H-NMR:

| function | group | δ (ppm) | mult. | J (Hz) | number of prot. |
|---|---|---|---|---|---|
| Mse | CH$_3$— | 2.97 | S | — | 3 |
|  | β-CH$_2$— | Disappeared under residual water of DMSO—d$_6$. | | | |
|  | α-CH$_2$— | 4.08 | "Sext." | $^3J_{H-H}$, 5.5 $^3J_{P-H}$, 7 | 4 |
| Aryl | Aryl- | 7.78 | 2x D | $^3J_{H-H}$, 9.0 | 4 |
| NH$_4$+— | (NH$_3$D)+ | 7.26 | S, broad | — | 3 |

IR:

| function | group | wave number (cm$^{-1}$) and strength |
|---|---|---|
| Mse- | —SO$_2$— | 1315 (W) and 1135 (S) |
| Aryl | Aryl-H | 1595 (S) |
|  | Aryl-NO$_2$ | 1515 (S) and 1350 (S) |
| Phosphate | P=O | 1255 (S) |
|  | P—O—Aryl | 1173 (W) |
|  | P—O—Alkyl | 1035 (S) |
| NH$_4$+— | NH$_4$+— | 1440 (M) and 1420 (M) |

9. DETERMINATION OF THE CATALYTIC ACTIVITY OF WATER IN THE DEPROTECTION WITH NH$_3$ GAS (CHROMATOGRAPHIC)

Ingredients

Ammonia gas, NH$_3$ was dried by condensing the gas in a three-neck flask cooled to −78° C. (acetone/dry ice), and thereafter carefully adding pieces of sodium metal until the liquid was fully deep-blue in colour.

Procedure

In four separate experiments, 12 ml of a 1% (w/v) solution of bis-(Mse)-paranitrophenyl phosphate in dry acetonitrile was introduced into a 50 ml three-neck flask. This flask was equipped with a gas inlet tube and a calcium chloride tube. Subsequently, gaseous ammonia was passed through the solution by allowing a quantity of condensed gas to evaporate.

Before the introduction of gas was started, however, 0.01% of water had been added to the acetonitrile solution in the first experiment, 0.2% of water in the second, and 2% of water in the third (percentages are by volume).

The control experiment was carried out under fully dry conditions.

The course of the deprotection was monitored by taking 2 μl samples at 0, 1.5, 5, 10, 15 and 30 minutes, measured after the beginning of the reaction, and transferring these to a kiesel gel plate.

Mobile phase A: $R_f$ values: bis-(Mse)-paranitrophenyl phosphate: 0.78, mono-(Mse)-paranitrophenyl phosphate, NH$_4$ salt: 0.24.

The thin-layer chromatograms show that the addition of larger quantities of water caused faster deprotection. When 2% by volume of water was used, a significant selective deprotection was realized after a period as short as 5 minutes, while after 30 minutes almost no bis-(Mse)-paranitrophenyl phosphate was found any longer.

10. SYNTHESIS OF BIS-(MSE)-PARANITROBENZYL PHOSPHATE (FIG. 16).

Ingredients

Paranitrobenzyl alcohol, MW: 153.13, was purified as follows:

20 g of the material was dissolved at 80° C. in 500 ml of a 9:1 mixture of water and methanol, whereafter 20 g Norit (activated charcoal) was added and the mixture was stirred for an additional 30 minutes at 80° C. Thereafter Norit was filtered off over Cellite (Hyflo"). From the clear, light-yellow filtrate, paranitrobenzyl alcohol crystallized in light-yellow needles. Prior to use, the material was dried on P$_2$O$_5$ in vacuo at room temperature (care being taken that no sublimation took place). Melting range after drying: 96°–97° C.

Procedure

To a solution of 0.750 g (0.0049 mole) of paranitrobenzyl alcohol in 4 ml dry pyridine in a 50 ml bulb flask, 1.838 g (0.0056 mole) of bis-(Mse)-phosphochloride was added very fast with stirring at room temperature, whereafter the flask was rapidly closed. The reaction was chromatographically monitored by very rapidly taking a 50 μl sample from the solution with a Hamilton microsyringe at given intervals, and, after dilution with 1 ml methanol, transferring this sample to a kiesel gel plate. (Mobile phase C: Paranitrobenzyl alcohol: $R_f$=0.76; bis-(Mse)-paranitrobenzyl phosphate: $R_f$=0.44).

After stirring for 20 minutes, the reaction was completed, and pyridine was removed in a rotary evaporator, followed by an oil pump vacuum (0.1 mm Hg) for 1 hour. The residue, a yellow oil, was brought to crystallization by scratching with a spatula. Recrystallization from water/methanol, 9:1, produced large, very pale yellow needle-shaped crystals.

Bis-(Mse)-paranitrobenzylphosphate (MW: 445.4): Yield: 2.13 g (0.00483 mole), 90% (on the basis or p-nitrobenzyl alcohol). Melting range: 85°–88° C. $R_f$ value in mobile phase: B: 0.31; C: 0.44. Elemental analysis: C: 35.17–35.27 H: 4.41–4.53 N: 3.13–3.15. Theory: C: 35.06 H: 4.53 N: 3.14 $^1$H-NMR:

| function | group | δ (ppm) | mult. | J (Hz) | number of prot. |
|---|---|---|---|---|---|
| Mse | CH$_3$— | 3.03 | S | — | 6 |
| | β-CH$_2$— | 3.50 | T | $^3J_{H-H}$, 5.5 | 4 |
| | α-CH$_2$— | 4.52 | "Sext." | $^3J_{H-H}$, 5.5 $^3J_{P-H}$, 7.0 | 4 |
| Benzyl | —CH$_2$— | 5.28 | D | $^3J_{P-H}$, 7.0 | 2 |
| | 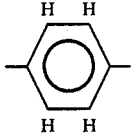 | 7.98 | 2 × D | $^3J_{H-H}$, 9.0 | 4 |

$^{31}$P-NMR:

| nucleus | δ (ppm) | mult. | J (Hz) |
|---|---|---|---|
| $^{31}$P,proton-uncoupled | 72.46 | S | — |
| $^{31}$P,proton-uncoupled | 72.46 | Quintet | $^3J_{H-P}$, 7.0 |
| $^{31}$P,TMP standard proton-uncoupled | 76.92 | S | — |

IR:

| function | group | wave number(cm$^{-1}$) and strength |
|---|---|---|
| Mse- | —SO$_2$— | 1320 (M) and 1130 (S) |
| Benzyl- | benzyl-H | 1608 (M) |
| | benzyl-NO$_2$ | 1515 (S) and 1350 (S) |
| Phosphate | P=O | 1290 (S) |
| | P—O—benzyl | 1193 (M) |
| | P—O—alkyl | 1040 (S) |

11. SYNTHESIS OF BIS-(MSE)-PHOSPHOMORPHOLIDATE (FIG. 17)

Ingredients

Morpholine was dried on NaOH pellets.

Procedure

To a solution of 1.644 g (0.0050) bis-(Mse)-phosphochloridate in 12.8 ml dry acetonitrile, a solution of 0.957 g (0.011 mole) of dry morpholine in 5 ml dry tetrahydrofuran was added dropwise with magnetic stirring at room temperature. Halfway the addition, a white precipitate of morpholine-HCl precipitated from the solution. After the addition of all morpholine over 10 minutes, the mixture was stirred for another 20 minutes at room temperature. Filtration of the morpholino-HCl precipitate and evaporation of the resulting filtrate produced 2.05 g of a yellow oil which after being kept at 4° C. for some time crystallized spontaneously. Recrystallization from absolute ethanol produced 1.68 g of white needle-shaped crystals.

Bis-(Mse)-phosphomorpholidate: (MW: 379.4). Yield: 1.68 g (0.0043 mole), 89% (on the basis of compound having the formula shown in FIG. 7. Melting range: 63°–67° C. Elemental analysis: C: 31.67–31.74 H:

5.86–5.87 N: 3.60–3.71. Theory: C: 31.66 H: 5.85 N: 3.69.

$^1$H-NMR:

| function | group | δ (ppm) | mult. | J (Hz) | number of prot. |
|---|---|---|---|---|---|
| Mse— | CH$_3$— | 3.03 | S | — | 6 |
| | β-CH$_2$— | 3.18 | T | $^3J_{H-H}$, 5.5 | 4 |
| | α-CH$_2$— | 4.41 | "Sext." | $^3J_{H-H}$, 5.5 $^3J_{P-H}$, 7 | 4 |
| Morpholino | —N⌒O⌒ | 3.60 | multiplet | — | 8 |

IR:

| function | group | wave number (cm$^{-1}$) and strength |
|---|---|---|
| Mse- | —SO$_2$— | 1320 (S) and 1140 (S) |
| Morpholino | —CH$_2$— | 1460 (M) |
| Phosphate | P=O | 1290 (S) |
| | P—O—alkyl | 1015 (S) |

Figure 18:
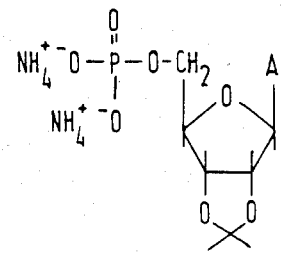

12. SYNTHESIS OF 2,3-O-ISOPROPYLIDENE-ADENOSINE-5'-MONOPHOSPHATE, BIS-NH$_4$$^+$ SALT (FIG. 18)

Requisites 2,3-O-Isopropylidene-adenosine, MW: 307.24, commercially available, was dried in vacuo at 110° C. over P$_2$O$_5$ for 3 hours just prior to use.

Silica gel column: 160 g silica gel (70–230 Mesh, Merck) was stirred into mobile phase A and after deaeration stacked in a column with a diameter of 6 cm. Bed height thereafter was 20 cm. Prior to use the column was rinsed with one column volume of A (700 ml).

Triethylammonium bicarbonate (TEAB) buffer: 40.48 g (0.40 mole) freshly-distilled triethylamine (Baker) was introduced into 1 l of distilled water, and the mixture was adjusted to pH 8.0 by passing CO$_2$ through it. (The buffer was prepared just before use and used once only).

DEAE-A25 column: DEAE-A25 (Sephadex) was introduced into 0.40M TEAB buffer and stacked in a column with a diameter of 3 cm and an ultimate bed height of 30 cm. Subsequently the column was rinsed for 24 hours with 0.01M TEAB buffer, pH 8.0, flow rate 20 ml per hour.

Dowex-50W-X2 column: Dowex-50W-X2 (200–400 Mesh) was equilibrated on a G-3 glass filter a few times and washed with:

(1) 2N HCl; (2) distilled water; (3) 2N NaOH; (4) distilled water. Thereafter the ion exchanger was brought into the NH$_4$$^+$ form by washing and equilibrating it a few times with a 2N NH$_3$ solution. Thereafter it was washed several times with distilled water, whereafter the ion exchanger was stacked in a column having a diameter of 3 cm and an ultimate bed height of 20 cm.

Procedure

To a solution of 1.536 g (0.0050 mole) of 2,3-O-isopropylidene adenosine in 20 ml dry pyridine, 1.80 g (0.0055 mole) of bis-(Mse)-phosphochloridate was added at room temperature with magnetic stirring. After stirring for 20 minutes, pyridine was removed in the rotary evaporator at 40°–50° C., whereafter the residue, a viscous, clear oil, was connected to the oil pump vacuum for another 2.5 hours to remove the last residues of pyridine.

Figure 19:
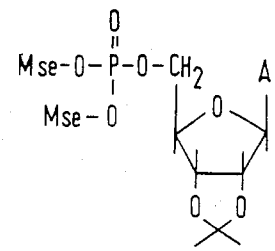

Thin-layer chromatographic check of the oil in agent A produced: (1) pyridine-HCL: R$_f$=0–0.3; (2) 2,3-o-isopropylidene adenosine-5'-bis-(Mse)-monophosphate (FIG. 19): R$_f$=0.37; 2,3-O-isopropylidene-adenosine (starting material): R$_f$=0.57.

Figure 20:
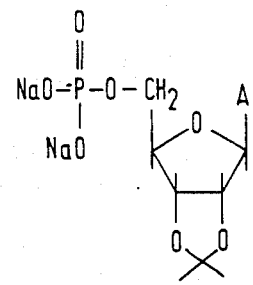
Figure 21:
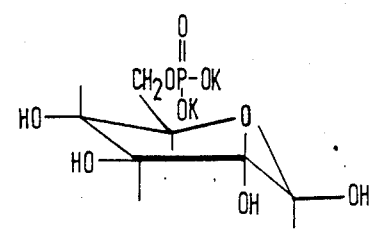
Figure 22:
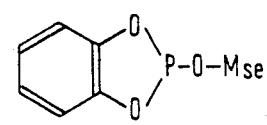

For purification, the oil was subjected to silica gel-column chromatography in agent A. At a flow rate of 4–5 ml/minutes, fractions of about 12 ml were collected. After having eluted 250 ml of the column, a small quantity of starting material appeared, and after 400 ml elution chromatographically pure 2,3-O-isopropylidene-adenosine-5'-bis-(Mse)-phosphate (FIG. 19) appeared in a total volume of 300 ml A. Evaporation of this eluate produced 2.62 g (0.00435 mole) crystalline compound having formula 16, 87%. It was deprotected as follows:

2.61 g (0.00435 mole) of the material was dissolved in 40 ml methanol, whereafter 6 ml 4N NaOH solution (4.5 equivalents base) were added with stirring at room temperature. After stirring for 1 minute, the solution was adjusted to pH 6 with acetic acid. Evaporation of the solution produced a viscous oil which after repeated washing with isopropyl alcohol and isopropyl ether become crystalline. The resulting 2,3-O-isopropylidene-adenosine-5'-monophosphate, bis Na$^+$ salt (FIG. 20) had an R$_f$ value of 0.48 in agent D. The yield was 2.25 g (0.00522 mole), i.e. 120% on the basis of the compound having the formula shown in FIG. 19. This can be explained from the sodium acetate present in the material. The further purification procedure of the compound having the formula shown in FIG. 20 was as follows:

The total quantity of material, 2.25 g, was dissolved in 0.01M TEAB buffer, pH 8.0, and transferred to a DEAE-A25 column, whereafter the latter was rinsed for 3 hours with the buffer last mentioned at a flow rate of 20 ml/hour. Elution of the column was effected with a 300 ml/300 ml linear gradient of 0.01→0.4M TEAB, pH 8.0 at a flow rate of 30 ml/hour; 6 ml fractions were collected and the elution of the column was monitored with a U.V. detection unit. When about 320 ml of the gradient had been passed through the column, the strength of the gradient was 0.2M TEAB, and a U.V. absorbing substance was detected. After complete elution the substance was in 300 ml TEAB buffer. This was evaporated and TEAB removed by repeatedly dissolving the residue in water and removing the water in the rotary evaporator. The ultimate residue, a quantity of white crystals, was re-dissolved in 50 ml distilled water and dry frozen. The resulting white crystals consisted of the triethylammonium salt of the compound having the formula shown in FIG. 20, and were chromatographically pure.

After being dissolved in distilled water, the substance was passed over a column of Dowex 50W-X2, ammonium form, and dry-frozen.

2,3-O-isopropylidene-adenosine-5'-monophosphate, bis-NH$_4$$^+$ salt, (MW: 421.36): Yield: 1.454 g (0.00345 mole), 69% (Basis: protected adenosine). $^1$H-NMR:

| function | group | δ (ppm) | mult. | number of prot. |
| --- | --- | --- | --- | --- |
| adenine— ND₂, with structure showing N, N, C—H(1), H(2), N, N | H₁ | 8.22 | S | 1 |
| | H₂ | 7.93 | S | 1 |
| ribose— with —CH₂—O, H(4) (4)H, H H, (4) (3), O O | —CH₂— | 3.93 | T | 2 |
| | H₃ | 6.03 | D | 2 |
| | H₄ | 4.83–5.3 | multiplet | 3 |
| isopropylidene H₃C CH₃ | —CH₃— | 1.50 | 2 × S | 6 |

13. SYNTHESIS OF β-D-GLUCOSE-6-PHOSPHATE, BIS-K+ SALT (FIG. 21)

Requisites 1.2.3.4-terta-acetyl-β-D-glucose, MW: 348, commercially available, was dried in vacuo over $P_2O_5$ at 60° C. for 3 hours just prior to use.

Procedure

To a solution of 0.612 g (0.00176 mole) of 1,2,3,4-tetra-acetyl-β-D-glucose in 5 ml dry pyridine, 0.678 g (0.00206 mole) of bis-(Mse)-phosphochloridate was added at room temperature with stirring. After stirring for 30 minutes, pyridine was removed in the rotary evaporator at 40°–50° C. Subsequently, the crude oil was dissolved in 50 ml methanol and introduced into a centrifuge tube, whereafter 3.6 ml of 4N KOH solution (9 equivalents of base) were added with magnetic stirring, whereby a precipitate was formed immediately. After 20 seconds the base was quenched with 3 equivalents of acetic acid, and the precipitate was centrifuged off, 2 minutes, 3000 rpm (Labofuge 6000).

After the removal of the supernatant the pellet was washed twice with methanol.

β-D-Glucose-6-phosphate, bis-K+ salt (MW: 351.3) Yield: 0.470 g (0.00134 mole), 76%. Hygroscopic substance, just like the commercial bis-Na+ of SIGMA. ¹H-NMR: Identical to that of the bis-Na+ salt of SIGMA.

IR: Identical to that of the bis-Na+ salt of SIGMA.

14. SYNTHESIS OF MSE-PHOSPHODICHLORIDITE (FIG. 8)

To 66.3 g (0.483 mole) freshly distilled $PCl_3$ in a 500 ml three-neck flask, equipped with a gas-tight sliding bearing and reflux condenser with tapping facility, 10 g (0.0805 mole) Mse-OH was added dropwise at room temperature and vigorous stirring over two hours. As Mse-OH is not immediately dissolved in $PCl_3$, a two-phase system was formed. Halfway the addition (after about 1 hour) some HCl began to escape from the solution.

After the addition of all Mse-OH, the mixture was refluxed on a paraffin bath at 90°–110° C. with vigorous stirring until no more HCl escaped (approx. 3–3.5 hours). Thereafter the temperature of the paraffin bath was raised to a maximum value of 120° C., whereafter (still with stirring) the excess of $PCl_3$ was drawn off from the reflux condenser (this $PCl_3$ was kept).

The turbid residue in the flask was rapidly transferred to a 250 ml flask, whereafter residues of $PCl_3$ and HCl were removed in a rotary evaporator and by means of oil pump vacuum. Subsequently the turbid oil, which gave a violent reaction with water, was transferred in portions of 3 g to 25 ml round-bottom flasks, which were well-sealed and stored at −18° C. Just prior to use, a 3 g portion was distilled in vacuo in a "Kugelrohr" distillation unit. This produced two fractions: fraction 1, distilled at 160° C. and 0.1 mm Hg, and fraction 2, 200° C. and 0.1 mm Hg. As on the basis of the ¹H-NMR spectrum, fraction 1 contains more impurities than fraction 2, the latter fraction was used in further reactions.

Mse-phosphodichloridite (MW: 225.12) Yield after distillation, fraction 2: 94% × 60% 56%. ¹H-NMR fraction 2:

| function | group | (ppm) | mult. | J (Hz) | number of prot. |
| --- | --- | --- | --- | --- | --- |
| Mse- | —CH₃ | 2.72 | S | — | 3 |
| | β-CH₂— | 3.17 | T | $^3J_{H-H}$, 5.5 | 2 |
| | α-CH₂— | 4.33 | distorted sextet | $^3J_{H-H}$, 5.5; $^3J_{P-H}$, 8 | 2 |

15. SYNTHESIS OF O-PHENYLENE-MSE-PHOSPHITE (FIG. 22)

Pyrocatechol(1,2-dihydroxybenzene), MW: 110.11, was dried at room temperature in vacuo over $P_2O_5$ just prior to use.

To a solution of 1.59 g (0.00706 mole) of Mse-phosphodichloridite in 25 ml dry tetrahydrofuran, cooled at −78° C., a solution of 0.78 g (0.00708 mole) of pyrocatechol and 1.15 ml (0.0142 mole) of pyridine in 80 ml dry tetrahydrofuran was slowly added with magnetic stirring, whereby a viscous, white precipitate was formed immediately. After 15 minutes all of the pyrocatechol solution had been added, and the mixture was warmed up to room temperature over a period of one half hour.

Subsequently, 250 ml of ethylacetate, followed by 100 ml of distilled water, was added to the mixture. After shaking in a separating funnel, the ethylacetate layer was processed and evaporated to a white crystal mass. Re-crystallization of this residue from toluene produced 1.72 g white crystals.

O-phenylene-Mse-phosphite Yield: 1.72 g (0.00656 mole), 93%. Melting range: 97°–104° C. ¹H-NMR:

| function | group | δ (ppm) | mult. | J (Hz) | number of prot. |
| --- | --- | --- | --- | --- | --- |
| Mse— | CH₃ | 2.88 | S | — | 3 |
| | β-CH₂— | 3.08 | T | $^3J_{H-H}$, 5.5 | 2 |
| | α-CH₂ | 3.96 | "Sext." | $^3J_{H-H}$, 5.5; $^3J_{P-H}$, 6 | 2 |

| function | group | δ (ppm) | mult. | J (Hz) | number of prot. |
|---|---|---|---|---|---|
| Phenylene | 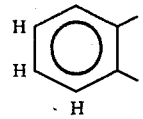 | 7.0 | S | — | 4 |

Figure 16:
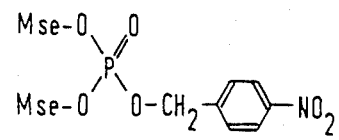
Figure 17:
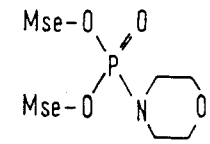

16. SYNTHESIS OF BIS-(MSE)-PARANITROBENZYL PHOSPHATE (FIG. 16), VIA MSE-PHOSPHODICHLORITE 2.80 g (0.0124 mole) freshly distilled Mse-phosphodichloridite, dissolved in 15 ml dry tetrahydrofuran, was introduced into a 500 ml three-neck flask equipped with three 50 ml drop funnels. After cooling this solution to −78° C., a solution of 1.29 g (0.0104 mole) of Mse-OH and 0.85 ml (0.0104 mole) of pyridine in 30 ml dry tetrahydrofuran was added dropwise with vigorous stirring in a period of 5 minutes, whereafter stirring was continued for another 10 minutes. Subsequently, a solution of 1.59 g (0.0104 mole) of paranitrobenzyl alcohol and 0.85 ml (0.0104 mole) of pyridine in 30 ml tetrahydrofuran was added dropwise to the resulting mixture in a period of 8 minutes. After stirring for another 20 minutes, the solution was warmed up to room temperature, whereafter 200 ml ethyl acetate and 50 ml 0.5 NaHCO₃ solution were added to the solution. While the thus resulting two-phase system was vigorously stirred at room temperature, a solution of 3.12 g (0.0124 mole) of iodine in ethyl acetate was slowly added dropwise. The reduction of the iodine by the phosphites present in the solution was immediately seen from the rapid disappearance of the dark-brown iodine colour in the two-phase system. After 15 minutes the oxidation reaction was completed, and the contents of the flask were transferred to a separating funnel, whereafter ethyl acetate layer and aqueous layer were separated.

Subsequently, the dark-browm ethylacetate layer was stripped off iodine by shaking with an aqueous NaHSO₃ solution to decolorization. Further processing and evaporation of the ethylacetate layer produced 2.8 g of yellow oil. A chromatographic check of this oil in eluent B caused 2 U.V.-positive fractions to be distinguished: one fraction with $R_f$=0.310 (equal to the $R_f$ value of bis-(Mse)-paranitrobenzyl phosphate in this eluent system) and one fraction with $R_f$ value 0.46 (which is equal to that for paranitrobenzyl alcohol).

The oil was dissolved in eluent B and passed over a silica gel column (diameter 6 cm, bed height 20 cm, flow rate 4–5 ml/minutes, size of fraction 8–12 ml.). Fractions 24–34 contained the substance with the higher $R_f$ value, and fractions 36–54 that with the lower value. Evaporation of the latter series of fractions produced 1.20 g of yellow oil which after washing with water solidified. Re-crystallization from methanol produced 1.10 g very pale yellow crystals of bis-(Mse)-paranitrobenzyl phosphate.

Bis-(Mse)-paranitrobenzyl phosphate Yield: 1.10 g (0.00247 mole), 20% (on the basis of the compound having the formula shown in FIG. 8. Melting range: 85°–86.5° C. The mixed melting range of a 1:1 mixture of the substance here synthesized and the paranitrobenzyl ester synthesized earlier via the compound having the formula shown in FIG. 7 which had a melting range of 85°–88° C., was 85°–87° C. ¹H-NMR:

| function | group | δ (ppm) | mult. | J (Hz) | number of prot. |
|---|---|---|---|---|---|
| Mse— | —CH₃ | 3.03 | S | — | 6 |
| | β-CH₂— | 3.46 | T | ³J_{H-H} 5.5 | 4 |
| | α-CH₂— | 4.55 | "Sext." | ³J_{H-H} 5.5 ³J_{P-H} 7 | 4 |
| Benzyl | —CH₂— | 5.25 | D | ³J_{P-H} 7 | 2 |
| | 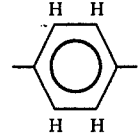 | 7.92 | 2 × D | ³J_{H-H} 9 | 4 |

Evaporation of the first series of fractions produced 0.9 g of yellow oil which after the addition of water became crystalline. Re-crystallization from ispropyl alcohol gave 0.33 g of very pale yellow crystals of Mse-bis-(paranitrobenzyl)phosphate.

Mse-bis-(paranitrobenzyl)phosphate Yield: 0.33 g (0.00069 mole), 5.6% (on the basis of the compound having the formula shown in FIG. 8. Melting range: 77°–78° C. $R_f$ value in eluent B: 0.46. ¹H-NMR:

| function | group | δ (ppm) | mult. | J (Hz) | number of prot. |
|---|---|---|---|---|---|
| Mse- | —CH₃ | 3.00 | S | — | 3 |
| | β-CH₂— | 3.40 | T | ³J_{H—H} 5.5 | 2 |
| | α-CH₂— | 4.57 | | ³J_{H—H} 5.5 ³J_{P—H} 6 | 2 |
| Benzyl- | —CH₂— | 5.25 | D | ³J_{P—H} 6 | 4 |
| | | 7.90 | 2x D | ³J_{H—H} 9 | 8 |

We claim:

1. A phosphorylating agent having the formula:

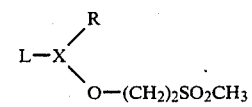

wherein

X is P or P=O;

L is a leaving group; and

R is a leaving group L, or —O—(CH₂)₂SO₂CH₃.

2. The phosphorylating agent of claim 1 wherein the leaving group L is selected from the group consisting of chlorine, 1,2,4-triazolyl, tetrazolyl, phthalimidooxy, succinimidooxy, and benzotriazolooxy.

3. The phosphorylating agent having the formula:

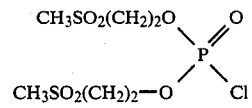

4. The phosphorylating agent having the formula:

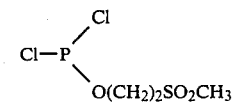

* * * * *